United States Patent
Mistry et al.

(10) Patent No.: US 11,717,471 B2
(45) Date of Patent: Aug. 8, 2023

(54) HYDROGEL MICROCAPSULES

(75) Inventors: Kishor Kumar Mistry, West Yorkshire (GB); Abdul Wahab Hussain, Bradford (GB); Petra Helga Beck, Camberley (GB); David Vaughan Palmer, Horsham (GB); Benjamin Roger Sales, Wilmborne (GB); Andrew Mint, Farnborough (GB)

(73) Assignee: ISP Investments LLC, Wilmington, DE (US)

( * ) Notice: Subject to any disclaimer, the term of this patent is extended or adjusted under 35 U.S.C. 154(b) by 350 days.

(21) Appl. No.: 13/990,890

(22) PCT Filed: Dec. 1, 2011

(86) PCT No.: PCT/US2011/062898
§ 371 (c)(1),
(2), (4) Date: Jul. 30, 2013

(87) PCT Pub. No.: WO2012/075293
PCT Pub. Date: Jun. 7, 2012

(65) Prior Publication Data
US 2013/0302392 A1 Nov. 14, 2013

Related U.S. Application Data

(60) Provisional application No. 61/418,446, filed on Dec. 1, 2010.

(51) Int. Cl.
| | |
|---|---|
| *A61K 8/11* | (2006.01) |
| *A61Q 19/00* | (2006.01) |
| *A61K 8/81* | (2006.01) |
| *C09K 15/00* | (2006.01) |
| *C11B 9/00* | (2006.01) |
| *C11D 3/50* | (2006.01) |
| *A61Q 19/10* | (2006.01) |
| *A61Q 15/00* | (2006.01) |
| *A61Q 5/12* | (2006.01) |

(52) U.S. Cl.
CPC ............. *A61K 8/11* (2013.01); *A61K 8/8152* (2013.01); *A61Q 19/00* (2013.01); *C09K 15/00* (2013.01); *C11B 9/00* (2013.01); *C11D 3/505* (2013.01); *A61K 2800/10* (2013.01); *A61K 2800/412* (2013.01); *A61K 2800/56* (2013.01); *A61Q 5/12* (2013.01); *A61Q 15/00* (2013.01); *A61Q 19/10* (2013.01)

(58) Field of Classification Search
CPC .... A61K 8/11; A61K 8/8152; A61K 2800/10; A61K 2800/412; A61K 2800/56; A61Q 19/00; A61Q 15/00; A61Q 19/10; A61Q 5/12; C09K 15/00; C11B 9/00; C11D 3/505

See application file for complete search history.

(56) References Cited

U.S. PATENT DOCUMENTS

| | | | | |
|---|---|---|---|---|
| 395,398 | A | * | 1/1889 | Klein ...................... B62B 19/02 280/13 |
| 4,231,855 | A | * | 11/1980 | Hodgdon ............... B01D 61/46 204/630 |
| 2004/0166165 | A1 | | 8/2004 | Mistry et al. |
| 2004/0223933 | A1 | * | 11/2004 | Hiwatashi ............... A61K 8/046 424/70.11 |
| 2007/0224899 | A1 | * | 9/2007 | Dungworth et al. ......... 442/164 |
| 2010/0036020 | A1 | | 2/2010 | Zhao et al. |

OTHER PUBLICATIONS

International Search Report, PCT/US2011/062898, published on Jun. 7, 2012.

* cited by examiner

*Primary Examiner* — Matthew P Coughlin
*Assistant Examiner* — Thurman Wheeler
(74) *Attorney, Agent, or Firm* — William J. Davis; Nathalie Tietcheu

(57) ABSTRACT

The present application provides hydrogel microcapsules, particularly, canonized hydrogel microcapsules having improved substantivity. This application further relates to the use of hydrogel microcapsules for delivering encapsulated actives in a wide range of industries and applications including: agrochemicals, pharmaceuticals, cosmetics industry, personal care products, laundering detergents, homecare & cleaning products, dish washing detergents, oral care, dental care, textiles, paper, mining, oil industry, water treatment, adhesives, coatings, plastics, sealants, construction, paints, inks and dyes onto different substrate surfaces such as skin, hair, textiles.

8 Claims, 1 Drawing Sheet

Figure 1 - Microcapsules before cationizing (absence of hydrogel shell)
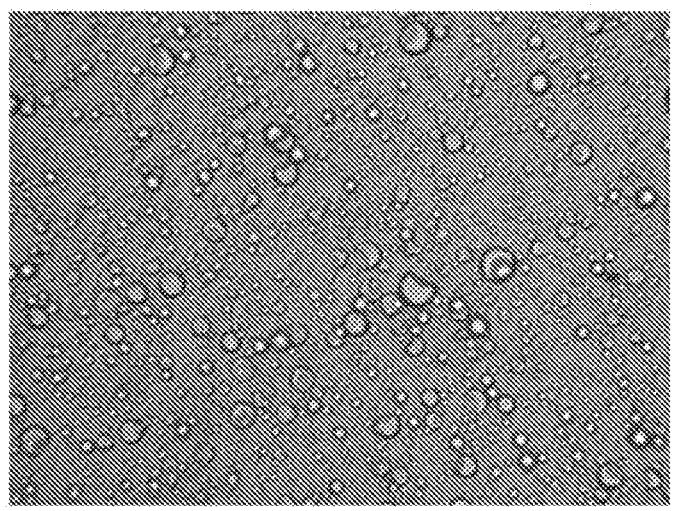
Figure 2 – Microcapsules after cationizing (presence of hydrogel shell)
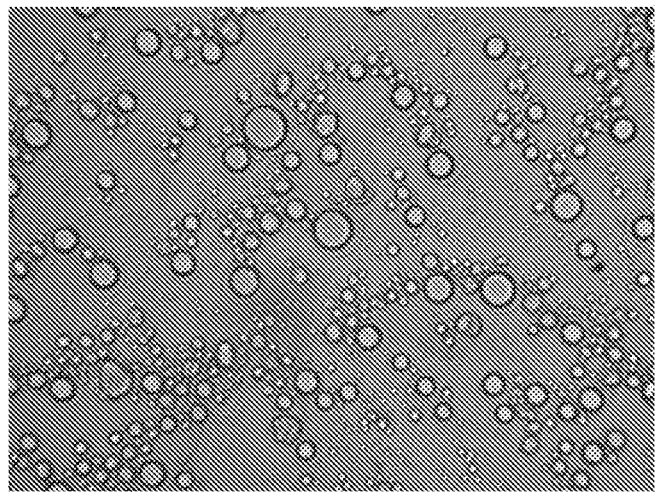

HYDROGEL MICROCAPSULES

CROSS REFERENCE TO RELATED APPLICATIONS

This application is the national stage of PCT Application No. PCT/US2011/062898 filed Dec. 1, 2011, which claims priority from Provisional Patent Application No. 61/418,446, filed Dec. 1, 2010, the entire disclosures of which are hereby incorporated in their entirety.

BACKGROUND

The present application relates to hydrogel microcapsules, particularly, cationized hydrogel microcapsules having improved substantivity. More particularly, the present application relates to substantive cationized hydrogel microcapsules comprising a lipophilic core material and a polymeric shell material, wherein the polymeric shell comprises: a) 5-99.9% by weight oil soluble mono functional ethylenically unsaturated amine monomer of Formula I, b) 0.1-95% by weight of polyfunctional ethylenically unsaturated monomer, and c) up to 30% by weight of other monomers. The present application also relates to the process for making hydrogel microcapsules as described herein.

The present application further relates to the use of hydrogel microcapsules for delivering encapsulated actives. Examples of actives include, without limitation, agrochemicals, pharmaceuticals, cosmetics industry, personal care products, laundering detergents, homecare & cleaning products, dish washing detergents, oral care, dental care, textiles, paper, mining, oil industry, water treatment, adhesives, coatings, plastics, sealants, construction, paints, inks and dyes onto different substrate surfaces such as skin, hair, textiles. The delivery system described herein can be advantageously used to impart a long lasting delivery of actives on a substrate.

Encapsulation processes have been widely described. The preparation and use of core-shell particles or so called microcapsules is also known. Generally, the main objectives behind the designing of microcapsules are:
(a) providing protection and stability to entrapped actives in such systems;
(b) controlling the release rate of entrapped actives;
(c) providing a delivery-matrix for targeted delivery of such active molecules;
(d) providing means of improved substantivity of actives on a particular surface or substrate.

There are number of microencapsulation methods for preparing and delivering actives using such microcapsules. The known methods include coacervation, spray drying, interfacial polymerisation and in situ polymerization. The microcapsule particles formed have an inner core material surrounded by an outer polymeric shell in which the core contains hydrophobic materials.

In the microencapsulation process utilizing the in situ polymerisation method, the microcapsule shell is formed by polymerizing mixtures of acrylates, methacrylates, vinyl or allyl monomers having ethylenically unsaturated groups. In general, the method involves dissolving the monomers in the hydrophobic core material and forming an oil-in-water emulsion and then the monomers are polymerized by free radical initiation to form the outer polymeric microcapsule shell.

Documents describing the preparation of microcapsules by in situ polymerisation of unsaturated ethylenically monomers include Japan Synthetic Rubber Company (U.S. Pat. No. 4,798,691), BASF (U.S. Pat. No. 5,292,835, US2003118822, US2009289216, US2010068525, WO2009077525, WO2009090169), Ciba (US2003018102, US2007224899, US2010003518, WO2008058868), Appleton Papers (US2009274906) and Akzo Nobel (US2007208093).

U.S. Pat. No. 4,798,691 assigned to Japan Synthetic Rubber Company describes microcapsule formation by polymerising blends of monomers having ethylenically unsaturated groups. The monomer blends comprise crosslinkable monomer, hydrophilic monomer and another monomer which is capable of co-polymerising with the crosslinkable and hydrophilic monomer.

U.S. Pat. No. 5,292,835 assigned to BASF discloses composition, process and use of microcapsules made by in situ polymerization. Specifically disclosed are polymerising monomer mixtures of A) 30-100% by weight of one or more $C_1$-$C_{24}$-alkyl esters of acrylic or methacrylic acid (monomers 1), B) 0-70% by weight of a bi- or polyfunctional monomer (monomer II). Specifically illustrated are polymerisation reactions of acrylate monomers such as methyl methacrylate, methacrylic acid and butanediol diacrylate together with a free radical initiator.

US application No. 2007224899 filed by Ciba discloses microcapsules comprising a core material within a substantially impervious polymeric shell, wherein the core material comprises a hydrophobic substance and a polymeric shell comprising: A) 5 to 90% by weight of an ethylenically unsaturated water soluble monomer, B) 5 to 90% by weight of a multifunctional monomer, and C) 0 to 55% by weight other monomer, and wherein the amount of the polymeric shell and the proportions of A, B and C are such that the particles exhibit a half height of at least 350° C. The ethylenically unsaturated water soluble monomer has the water solubility of at least 5 gm/100 cc at 25° C. Specifically, the water soluble monomer methacrylic acid and microcapsules are incorporated into textile materials.

US application Nos. 2009274906, 20090274905, 20090274905 filed by Appleton Papers describe a multi-step method of microencapsulation and the microcapsules and the particles produced by the process. The applications disclose low permeability microcapsules prepared predominately from >95% multi-functional oligomers. The first process step involves a pre-polymer formation in an oil medium to form a first reaction product. This first reaction product is then used for the actual encapsulation process. The microcapsule shell formation involves an interaction of a first reaction product with an anionic emulsifier at the oil/water interface.

U.S. application No. 20070208093 filed by Akzo Nobel relates to thermally expandable thermoplastic microspheres comprising a polymer shell made from ethylenically unsaturated monomers encapsulating a propellant. The volatile propellant is removed to produce hollow polymer particles that are used for the manufacture of paper.

These encapsulation processes, while providing microcapsule systems that stabilize and provide a certain controlled release of actives, however do not provide a delivery matrix capable of improving the sustained release of actives particularly perfumes and oils from substrates. Now, in particular in the field of functional perfumery, for applications such as detergents or fabric softeners, the substantivity of such actives on a substrate such as a fabric constitutes an issue of paramount importance for the industry.

Other approaches in encapsulation technology target the controlled or customized release of actives from substrates.

These microcapsules are adapted to break under friction and provide an instant "burst" of the fragrance when the microcapsules are ruptured.

There are numerous patents relating to delivering fragrance microcapsules from detergent products, such as fabric softeners, rinse off products and shampoos. In a majority of the cases the microcapsules are based on melamine formaldehyde chemistry.

U.S. Pat. No. 4,145,184 describes detergent compositions that contain perfumes in the form of friable microcapsules. Preferred materials for the microcapsule shell walls are the aminoplast polymers comprising the reaction product of urea and formaldehyde.

U.S. application No. 20040071746 filed by International Flavors & Fragrances relates to a polymeric encapsulated fragrance is suitable for use in personal care and cleaning products. The fragrance is encapsulated by a first polymer material to form a fragrance encapsulated polymer, wherein the polymer encapsulated shell is then coated with a cationic polymer, preferably a cationic starch and guar U.S. application No. 20070123442 filed by Firmenich relates to a liquid product comprising dispersed perfumed capsules and a thickening system which is a combination of non-ionic with cationic polymers. This allows a prolonged storage of the perfuming capsules without alteration of the latter and without the need to shake the composition before use in order to obtain a homogeneous composition of capsules. This further allows improved deposition of both the fragranced microcapsules and the cationic conditioning polymers onto target surfaces from rinse-off products.

However, the current available microcapsules do not allow effective targeting and deposition onto the intended substrates such as textiles, skin or hair in their respective applications. Further, these microcapsules are predominately prepared from melamine formaldehyde or urea formaldehyde resins and the resulting microcapsules have an anionic outer surface charge. In order to change the negative charge the microcapsule outer shell surfaces are modified by addition of cationic materials either during or after the encapsulation process. However, these modifications still fail to deposit the microcapsules sufficiently onto the intended substrates and provide the controlled release of the encapsulated functional materials. Furthermore, the microcapsules manufactured from formaldehyde resins suffer from inherent residual toxic formaldehyde impurities. Moreover, the prior art encapsulation methods fail to provide effective encapsulations of all fragrance components.

It is desirable to have microcapsules with enhanced substantivity and also which are free of residual formaldehyde impurities.

Also desired are microcapsule compositions that can be effectively incorporated and deposited onto the intended substrate. It would be beneficial to be able to use these microcapsules to produce a delivery matrix for the substances, particularly, substances of a lipophilic nature, for example, fragrances.

Accordingly, the present application describes a microencapsulation process and composition comprising such polymers which do not require any post modification, and is directed to the preparation of cationic shell microcapsules directly. However, an optional post coating may be applied for further enhancement of substantivity.

The microcapsules described herein can release their core active contents by a number of release mechanisms such as swelling of the microcapsule shell, diffusion or physical rupture. Furthermore, in accordance with one aspect, the microcapsules of the present application can absorb water, swell and release the lipophilic substances. Another advantage associated with some aspects is that the post treatment or post modification of the microcapsules with cationic materials after the encapsulation can be bypassed.

SUMMARY

This application relates to hydrogel microcapsules, particularly, cationized hydrogel microcapsules having improved substantivity and capable of providing an efficient long lasting delivery matrix, the release of which can be designed to give either permanent encapsulation or triggered release of the core material.

The present application provides a substantive cationized hydrogel microcapsule comprising of a lipophilic core material and a polymeric shell material, wherein the polymeric shell comprises:
a) 5-99.9% by weight oil soluble mono functional ethylenically unsaturated amine monomer represented by Formula I:

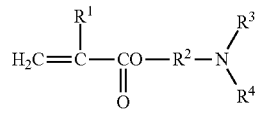

where $R^1$=H, $CH_3$; $R^2$=$C_{2-8}$ alkyl group; $R^3$ and $R^4$ independently=H, $C_{2-8}$ alkyl groups
b) 0.1-95% by weight of polyfunctional ethylenically unsaturated monomer, and
c) up to 30% by weight of other monomers.

In one embodiment, the polymeric shell comprises:
a)>50% by weight oil soluble mono functional ethylenically unsaturated amine monomer represented by Formula I:

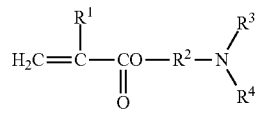

where $R^1$=H, $CH_3$; $R^2$=$C_{2-8}$ alkyl groups; $R^3$ & $R^4$ independently=H, $C_{2-8}$ alkyl groups,
b)<50% by weight of polyfunctional ethylenically unsaturated monomer.

The oil soluble mono functional ethylenically unsaturated amine monomer of Formula I may be selected from the group consisting of di-alkylaminoalkyl methacrylate, alkylaminoalkyl methacrylate, di-alkylaminoalkyl acrylate, di-alkylaminoalkyl acrylate, alkylaminoalkyl acrylate and combinations thereof. The amine groups on the polymeric shell are protonated or alkylated such that the shell imbibes water to form an outer cationic hydrogel shell.

The monomers of Formula I include, but are not limited to, tertiary-butylaminoethyl methacrylate (TBAEMA) n-Butylaminoethyl methacrylate (NBAEMA), Diethylaminoethyl methacrylate (DEAEMA), Dimethylaminoethyl methacrylate (DMAEMA), Diisopropylaminoethyl methacrylate (DPAEMA), Dibutylaminoethyl methacrylate (DBAEMA), Dipropylaminoethyl methacrylate (DPAEMA), Tertiary pentylaminoethyl methacrylate (TPAEMA), Tertiary hexylaminoethyl methacrylate (THAEMA), Tertiary-butylaminopropyl methacrylate (TBAPMA), Diethylaminopropyl methacrylate (DEAPMA), and Dimethylaminopropyl methacrylate (DMAPMA) or combinations thereof, listed in Table 1.

In accordance with certain aspects, the microcapsule composition may include monomer (a) in an amount from about 60 to 95% by weight of the polymer shell.

The polyfunctional ethylenically unsaturated monomer (b) may be selected from divinyl benzene, ethylene glycol di(meth)acrylate, di(ethylene glycol) di(meth)acrylate, triethylene glycol di(meth)acrylate, propylene glycol di(meth)acrylate, 1,4-butanediol di(meth)acrylate, 1,6-hexanediol di(meth)acrylate, glycerol di(meth)acrylate, 1,3-butanediol di(meth)acrylate, neopentyl glycol di(meth)acrylate, 1,10-decanediol di(meth)acrylate, pentaerythritol tri(meth)acrylate, pentaerythritol tetra(meth)acrylate, dipentaerythritol hexa(meth)acrylate, triallylformal tri(meth)acrylate, allyl methacrylate, trimethylol propane tri(meth)acrylate, tributanediol di(meth)acrylate, PEG 200 di(meth)acrylate, PEG 400 di(meth)acrylate, PEG 600 di(meth)acrylate, 3-acryloyloxyglycol monoacrylate, triacryl formal, triallyl isocyanate, triallyl isocyanurate and mixtures thereof.

In accordance with certain aspects, the microcapsule composition may include the polyfunctional monomer (b) in an amount from about 20 to 45% by weight of the polymer shell.

The microcapsule compositions may also include other monomers, stabilizers, initiators and other excipients.

The other monomers, i.e., monomer (c), include $C_1$-$C_{30}$ esters of ethylenically unsaturated carboxylic acid (e.g., acrylic acid or methacrylic acid), styrene, acrylonitrile, vinyl acetate, vinylpyridine, glycidyl acrylate, glycidyl acrylamide, methacrylamide, N-methylolacrylamide, N-methylolmethacrylamide, acrylic acid, methacrylic acid, itaconic acid, fumaric acid, 2-hydroxyethyl methacrylate, and 2-hydroxypropyl methacrylate or combinations thereof. Monomer (c) also includes those based on C1-C4 alkyl amino methacrylamide, for example: dimethyl aminopropyl methacrylamide, diethyl aminopropyl methacrylamide, dipropylaminopropyl acrylamide, dipropyl aminopropyl methacrylamide, dibutyl aminopropyl methacrylamide and dibutyl aminopropyl acrylamide. Also Monomer (c) includes quaternized acrylate and methacrylate monomers such as dimethylaminoethyl methacrylate quaternized with methyl chloride.

The microcapsules described herein may have a mean particle size of 1-2000 μm, more particularly 1-50 μm, and in some cases 1-20 μm.

The microcapsules of the present application may include the polymeric shell material at an amount of 1-50%; more particularly from 5-20% by weight of the microcapsules.

The present application also provides for the use of such microcapsule composition as a delivery matrix to deliver lipophilic core materials for a wide range of industries and applications. Examples of particular applications include without limitation: agrochemicals, pharmaceuticals, cosmetics industry, personal care products, laundering detergents, homecare & cleaning products, dish washing detergents, oral care, dental care, textiles, paper, mining, oil industry, water treatment, adhesives, coatings, plastics, sealants, construction, paints, inks and dye formulations.

In accordance with certain aspects, the lipophilic core material includes fragrances, UV absorbers, emollient oils, insecticides, phase change materials, dyes, detergents, printing inks, perfumes, silicone conditioners, shampoos, biocides, adhesives, corrosion inhibitors, anti-fouling agents, flavors, cosmetic actives, oxidizing agents, personal care actives, medicines, agrochemicals, fertilizers, fats, oils, nutrients, enzymes, liquid crystals, paints, rustproofing agents, recording materials, catalysts, chemical reactants and magnetic substances.

BRIEF DESCRIPTION OF THE DRAWINGS

FIG. 1 is a Light Micrograph showing Microcapsules before cationizing (absence of hydrogel shell).

FIG. 2 is a Light Micrograph showing Microcapsules after cationizing (presence of hydrogel shell).

DETAILED DESCRIPTION

The industry still requires improvements in the field of polymeric micro-encapsulation, and in particular, there is a need for a delivery system providing release of an active ingredient which is spread out over a more or less extended period of time. In other words, still needed is an encapsulation system that allows variable release of active ingredients, and therefore they may be suitable for utilization in applications wherein a customized or controlled release is required. Another area of improvement identified is in the need of efficient deposition on the substrate, so as to obtain the desired release from such substrate.

Usually, the core materials can be released from the microcapsules by several release mechanisms depending on the monomer mixture compositions. Microcapsules formed from high contents of amine monomers will release the inner core material preferably by osmotic release mechanism. For example, in surfactant formulations the hydrogel capsule shell exist in a less swollen form and on dilution with water, due to change in the ionic strength the microcapsule shell will swell and whereby release the internal core contents. Conversely, microcapsules having lower contents of amine monomer and higher multi-functional cross linker monomer will release the core contents by either diffusion and physical rupture mechanisms or combination of both. Without being bound by theories, the present application provides an efficient solution to the problems encountered in the prior art, by providing highly substantive cationized hydrogel microcapsules encasing a lipophilic core material with a polymeric shell primarily comprising oil soluble unsaturated amine monomer and a multifunctional crosslinker.

The microcapsules of the present application work on hydrogel mechanism, they absorb water, swell and release the lipophilic substances through various mechanisms as described above. Advantageously, the properties of the polymeric capsule shell can be designed to give either permanent encapsulation or triggered release of the core material. Another advantage of certain embodiments in the present application is direct cationization of the microcapsules thus excluding need of post treatment or post modification of the microcapsules with cationic materials after the encapsulation.

It is further contemplated that the majority of surfaces such as textiles, skin, teeth, hard surfaces and hair inherently have a negative charge associated on them and the microcapsules described herein, being cationically charged, have affinities for such negative charges by electrostatic attraction and thus provide excellent substantivity onto the substrate. Moreover, in accordance with certain aspects, the particles described herein may be prepared by a process which avoids any problem of contamination unlike what was the case in the prior art.

The oil soluble amine monomer useful in the practice of this invention can be represented by Formula I:

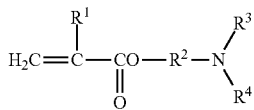

Where $R^1$=H, $CH_3$; $R^2$=$C_{2-8}$ alkyl group, $R^3$ and $R^4$ independently=H, $C_{2-8}$ alkyl group.

Particularly useful amine monomers of Formula I include, but are not limited to, di-alkylaminoalkyl methacrylate, alkylaminoalkyl methacrylate, di-alkylaminoalkyl acrylate, di-alkylaminoalkyl acrylate, and alkylaminoalkyl acrylate as described in Table 1.

In one embodiment, the monomer of Formula I may be Tertiary-butylaminoethyl methacrylate (TBAEMA) n-Butylaminoethyl methacrylate (NBAEMA), Diethylaminoethyl methacrylate (DEAEMA), Dimethylaminoethyl methacrylate (DMAEMA), Diisopropylaminoethyl methacrylate (DPAEMA), Dibutylaminoethyl methacrylate (DBAEMA), Dipropylaminoethyl methacrylate (DPAEMA), Tertiary pentylaminoethyl methacrylate (TPAEMA), Tertiary hexylaminoethyl methacrylate (THAEMA), Tertiary-butylaminopropyl methacrylate (TBAPMA), Diethylaminopropyl methacrylate (DMAPMA), and Dimethylaminopropyl methacrylate (DMAPMA) or combination thereof.

TABLE 1

List of amine monomers represented by Formula 1:

Formula 1

$$H_2C=\underset{\underset{R^1}{|}}{C}-\underset{\underset{O}{\|}}{C}-R^2-N\overset{R^3}{\underset{R^4}{\diagdown}}$$

| Generic Name | Generic Formula | Examples |
|---|---|---|
| Di-alkylaminoalkyl methacrylate | Di- $R^3$ & $R^4$ amino $R^2$ methacrylate where $R^3$ = $R^4$ = alkyl group of $C_{1-8}$ | $R^3$ & $R^4$ = methyl (CH3) and $R^2$ = ethyl ($C_2H_5$) Dimethylaminoethyl methacrylate |
| | $R^2$ = alkyl group of $C_{2-8}$ | $R^3$ & $R^4$ = ethyl and $R^2$ = ethyl |
| | $R^1$ = methyl group ($CH_3$) | Diethylaminoethyl methacrylate |
| | | $R^3$ & $R^4$ = isopropyl and $R^2$ = ethyl |
| | | Diisopropylaminoethyl methacrylate |
| | | $R^3$ & $R^4$ = ethyl and $R^2$ = propyl |
| | | Diethylaminopropyl methacrylate |
| Alkylaminoalkyl methacrylate | $R^3$ & $R^4$ amino $R^2$ methacrylate where $R^3$ = H | $R^4$ = t-butyl [$C(CH_3)_3$] and $R^2$ = ethyl ($C^2H^5$) |
| | $R^4$ = alkyl group of $C_{3-8}$ | tertiary-Buylaminoethyl |
| | $R^2$ = alkyl group of $C_{2-8}$ | methacrylate |
| | $R^1$ = methyl group ($CH_3$) | |
| Di-alkylaminoalkyl acrylate | Di- $R^3$ & $R^4$ amino $R^2$ acrylate where $R^3$ = $R^4$ = alkyl group of $C_{2-8}$ | $R^3$ & $R^4$ = propyl ($C_3H_7$) and $R^2$ = propyl ($C_3H_7$) |
| | $R^2$ = alkyl group of $C_{3-8}$ | Di-propylaminopropyl acrylate |
| | $R^1$ = hydrogen (H) | |
| Alkylaminoalkyl acrylate | $R^3$ & $R^4$ amino $R^2$ acrylate where $R^3$ = H | $R^4$ = propyl ($C_3H_7$) and $R^2$ = propyl ($C_3H_7$) |
| | $R^4$ = alkyl group of $C_{3-8}$ | Propylaminopropyl acrylate |
| | $R^2$ = alkyl group of $C_{3-8}$ | |
| | $R^1$ = hydrogen (H) | |

These amine monomers can be present in an amount of about 5 to 99.9% by weight of the total polymer shell; more particularly >50% and still more particularly from about 60 to 95% by weight of polymer shell. This amount is sufficient to effectively produce the microcapsule of desired properties and strength.

The amine groups on the polymeric shell are protonated or alkylated with cationizing agents that imbibe water to form an outer cationic hydrogel shell. Cationizing agents include all conventionally used known in the literature. Particularly useful cationizing agents include inorganic acids such as hydrochloric acid, sulphuric acid, phosphoric acid, nitric acid; or organic acids ($C_1$ to $C_{18}$) such as of formic acid, acetic acid, propionic acid; or quaternizing reagents such as alkyl chlorides or aromatic chlorides; examples include methyl chloride, dimethyl sulphate, and benzyl chloride or combinations thereof.

The crosslinker includes polyfunctional ethylenically unsaturated monomer (b) which can be, for example, divinyl benzene, ethylene glycol di(meth)acrylate, di(ethylene glycol) di(meth)acrylate, triethylene glycol di(meth)acrylate, propylene glycol di(meth)acrylate, 1,4-butanediol di(meth)acrylate, 1,6-hexanediol di(meth)acrylate, glycerol di(meth)acrylate, 1,3-butanediol di(meth)acrylate, neopentyl glycol di(meth)acrylate, 1,10-decanediol di(meth)acrylate, pentaerythritol tri(meth)acrylate, pentaerythritol tetra(meth)acrylate, di pentaerythritol hexa(meth)acrylate, triallylformal tri(meth)acrylate, allyl methacrylate, trimethylol propane tri(meth)acrylate, tributanediol di(meth)acrylate, PEG 200 di(meth)acrylate, PEG 400 di(meth)acrylate, PEG 600 di(meth)acrylate, 3-acryloyloxyglycol monoacrylate, triacryl formal, triallyl isocyanate, and triallyl isocyanurate or combination thereof.

A particularly useful polyfunctional ethylenically unsaturated monomer (b) is 1,4-butanediol di(meth)acrylate.

The polyfunctional monomer may be present in an amount from about 0.1 to 95% by weight of the total polymer shell; more particularly <50% and still more particularly from about 20 to 45% by weight of polymer shell. This amount is sufficient to effectively produce the cross linking of the amine monomer.

The polymer shell composition may also include up to 30% by weight of the other monomers selected from the group consisting of $C_1$-$C_{30}$ esters of ethylenically unsaturated carboxylic acid selected from the group consisting of acrylic acid or methacrylic acid, styrene, acrylonitrile, vinyl acetate, vinylpyridine, glycidyl acrylate, glycidyl acrylamide, methacrylamide, N-methylolacrylamide, N-methylolmethacrylamide, acrylic acid, methacrylic acid, itaconic acid, fumaric acid, 2-hydroxyethyl methacrylate, and 2-hydroxypropyl methacrylate and combination thereof. Other monomers that may be included under (c) type include those based on C1-C4 alkyl amino methacrylamide for example: dimethyl aminopropyl methacrylamide diethyl aminopropyl methacrylamide, dipropylaminopropyl acrylamide, dipropyl aminopropyl methacrylamide, dibutyl aminopropyl methacrylamide and dibutyl aminopropyl acrylamide and quaternised acrylate and methacrylate monomers such as dimethylaminoethyl methacrylate quaternised with methyl chloride.

In one embodiment, a substantive cationized hydrogel microcapsule is disclosed wherein the microcapsule comprises a lipophilic core material and a polymeric shell material, wherein the polymeric shell comprises:
a) 5-99.9% by weight oil soluble tertiary-butylaminoethyl methacrylate (tBAEMA), and
b) 0.1-95% by weight of 1,4-butanediol di(meth)acrylate.

The polymeric shell may contain on its outer surface 1-25% by weight polyvinyl alcohol based on the polymer shell and the degree of cationisation of the amine group is 1-100%.

The microcapsules described herein typically have a mean particle size from about 1 to about 2000 µm; particularly from about 1 to about 50 µm; more particularly from about 1 to about 20 µm. Average particle size may be determined by a Malvern Particle Size analyzer according to the standard procedure described in the literature.

In accordance with certain embodiments, the microcapsules may include the polymeric shell material in an amount of 1-50%; more particularly from 5-20% by weight of the microcapsules.

The term "cationized hydrogel microcapsules" as used herein refers to the delivery system comprising positively charged microcapsules synthesized in situ. The hydrogel may be obtained by polymerizing or copolymerizing primarily oil soluble amine monomers which subsequently absorb water, swell and develop a positive charge at the surface.

The term "substantive" as used herein refers to the microcapsules that can effectively be deposited onto the respective substrate. Cationized hydrogel microcapsules are efficiently deposited on the substrates and/or surfaces (such as skin, hair or textiles). The deposition is directly attributable to electrostatic interactions between oppositely charged sites on the substrate (e.g., hair shaft or skin surface) and on the microcapsule.

These cationic hydrogel microcapsules are deposited with reversible electrostatic charge and on trigger release the entrapped core material. The trigger could be anything ranging from change in pH or temperature, or pressure or ionic strength or combinations thereof.

The release mechanism can be osmosis, diffusion or physical rupture or combinations thereof. Furthermore, the microcapsule composition shell can be designed to form permanent encapsulation of the lipophilic core material in some use applications.

The microcapsules may be further modified to ensure the customized release, instantaneous, controlled or long lasting release of the core material by addition of additional cross-linkers such as diepoxy compounds and polycarboxylic acid such as adipic acid that react with amine groups on the microcapsule shell. In one embodiment, anionic material, such as, anionic copolymers, may be added to form polyelectrolyte complexes with the amine groups. In yet another embodiment, strongly hydrophobic alkylating agent such as lauryl chloride may be used for limiting the hydrogel swelling in some surfactant formulations.

In one aspect, the process of making microencapsules comprises the steps of: a) dispersing under stirring oil soluble amine monomer in a medium wherein the corresponding polymer is not soluble, comprising an initiator, a cross-linking agent and at least one stabilizer, thus providing an emulsion; b) polymerizing the emulsion followed by c) cationizing the capsule shell by addition of acid or alkylating agents at a temperature typically between 10 and 90° C., and providing polymeric hydrogel microcapsules having the water content of at least about 15% by weight when fully hydrated.

The polymerization may be induced by any conventional polymerization conditions. Generally polymerization is effected by the use of suitable redox initiators and/or thermal initiators. In accordance with certain aspects, the polymerization may be started by employing a thermal initiator alone or in combination with other initiator systems, for instance redox initiators.

In one embodiment, the polymeric shell of the microcapsule may comprise blends of:
(a) 5-99.9% by weight oil soluble mono functional ethylenically unsaturated amine monomer,
(b) 0.1-95% by weight of polyfunctional ethylenically unsaturated monomer, and
(c) up to 30% by weight of other monomers. The shell may be prepared by a process including the following steps:
(1) preparing an oil phase comprising a mixtures of monomers and lipophilic core material;
(2) separately preparing an aqueous phase comprising an emulsifier and water;
(3) adding the oil phase to the aqueous phase under mechanical shear to form an oil-in-water emulsion;
(4) inducing radical polymerisation through an initiator,
(5) forming core-shell microcapsules as a dispersion in water, and
(6) cationizing the polymeric capsule shell by addition of cationizing agent.

The polymerisation step may be carried out by redox or thermal initiation at a temperature between 10 and 90° C.

Thermal initiators include any suitable initiator compound that releases radicals at an elevated temperature, for example, organic peroxides such as dialkyl peroxides, diacyl peroxides, peroxy esters, peroxy dicarbonates, or azo compounds. Suitable initiators include dicetyl peroxydicarbonate, di(4-tert-butylcyclohexyl) peroxydicarbonate, dioctanoyl peroxide, dibenzoyl peroxide, dilauroyl peroxide, didecanoyl peroxide, tert-butyl peracetate, tert-butyl perlaurate, tert-butyl perbenzoate, tert-butyl hydroperoxide, cumene hydroperoxide, cumene ethylperoxide, diisopropylhydroxy dicarboxylate, 2,2'-azobis(2,4-dimethyl valeronitrile), 2,2'-azobis(isobutyronitrile), 1,1'-azobis(cyclohexane-1-carbonitrile), dimethyl 2,2'-azobis(2-methylpropionate), 2,2'-azobis[2-methyl-N-(2-hydroxyethyl)propionamide].

An optional purification step follows, in order to remove unreacted monomers. The purification step is carried out by either addition of further initiators such as ammonium persulphate or by steam distillation.

Stabilizers/Emulsifier particularly include cationic cellulose derivatives, quaternized gums, polyethylene imine, cationic polyacrylates and polyacrylamides, polyacrylates, gelatin, quaternized protein hydrolysates, and quaternized amino silicones, hydroxyethyl cellulose and polyvinyl pyrrolidone and poly vinyl alcohol, styrene co-polymer with maleic anhydride or acrylic acid.

The composition described herein may be used effectively as a delivery matrix to deliver lipophilic core material suitable for a wide range of industries and consumer products such as: agrochemicals, pharmaceuticals, cosmetics industry, personal care products, laundering detergents, homecare & cleaning products, oral care, dental care, textiles, paper, mining, oil industry, water treatment, adhesives, coatings, coatings, plastics, sealants, construction, paints, inks and dye formulations.

Examples of lipophilic core material include fragrances, UV absorbers, emollient oils, insecticides, phase change materials, dyes, detergents, printing inks, perfumes, silicone conditioners, shampoos, biocides, adhesives, corrosion inhibitors, anti-fouling agents, flavors, cosmetic actives, oxidizing agents, personal care actives, medicines, agrochemicals, fertilizers, fats, oils, nutrients, enzymes, liquid crystals, paints, rustproofing agents, recording materials, catalysts, chemical reactants and magnetic substances or combination thereof can be used directly or dissolved or dispersed in the oily substance as used herein depending on the purpose of use.

The non-limiting list of such material includes:
Linear or branched hydrocarbons of different chain lengths and viscosities such as mineral oil, petrolatum, white oil (also known as paraffin oil), dodecane, isododecane, squalane, hydrogenated polyisobutylene, polybutene, polydecene, docosane, hexadecane, isohexadecane and other isoparaffins, which are branched hydrocarbons.

Alcohol, diol, triol or polyol esters of carboxylic or dicarboxylic acids, of either natural or synthetic origin having straight chain, branched chain and aryl carboxylic acids include diisopropyl sebacate, diisopropyl adipate, isopropyl myristate, isopropyl palmitate, myristyl propionate, cetyl lactate, myristyl lacate, lauryl lactate, $C_{12-15}$ alkyl lactate, dioctyl malate, decyl oleate, isodecyl oleate, ethylene glycol distearate, ethylhexyl palmitate (octyl palmitate), isodecyl neopentanoate, tridecyl neopentanoate, castoryl maleate, isostearyl neopentanoate, di-2-ethylhexyl maleate, cetyl palmitate, myristyl myristate, stearyl stearate, cetyl stearate, isocetyl stearate, dioctyl maleate, octyl dodecyl stearate, isocetyl stearoyl stearate, octyldodecyl stearoyl stearate dioctyl sebacate, diisopropyl adipate, cetyl octanoate, glyceryl dilaurate, diisopropyl dilinoleate and caprylic/capric triglyceride. Naturally occurring includes triglycerides, diglycerides, monoglycerides, long chain wax esters and blends of these. Examples for naturally derived ester-based oils and waxes include, but are not limited to, argan oil, corn oil, castor oil, coconut oil, cottonseed oil, menhaden oil, avocado oil, beeswax, carnauba wax, cocoa butter, palm kernel oil, palm oil, peanut oil, shea butter, jojoba oil, soybean oil, rapeseed oil, linseed oil, rice bran oil, pine oil, sesame oil, sunflower seed oil and safflower oil. Also useful are hydrogenated, ethoxylated, propoxylated and maleated derivatives of these materials, e.g. hydrogenated safflower oil, hydrogenated castor oil.

Cholesterol and its esters and derivatives, as well as natural materials comprising cholesterol derivatives such as lanolin and lanolin oil.

Phospholipids (e.g. lecithin), sphingophospholipids, ceramides and related materials.

$C_4$-$C_{20}$ alkyl ethers of polypropylene glycols, $C_1$-$C_{20}$ carboxylic acid esters of polypropylene glycols, and di-$C_8$-$C_{30}$ alkyl ethers. Also included are PPG-14 butyl ether, PPG-15 stearyl ether, diodyl ether, dodecyl octyl ether, and mixtures thereof.

Saturated and unsaturated fatty acids including but not limited to oleic, palmitic, isostearic, stearic, ricinoleic, linoleic and linolenic acid.

Carboxylic monoesters and polyesters of sugars (mono-, di- and polysaccharides) and related materials.

Silicones such as polyalkylsiloxanes, polydialkylsiloxanes, polydiarylsiloxanes, and polyalkarylsiloxanes may also be used. This includes the polydimethylsiloxanes, which are commonly known as dimethicones. Further cyclic siloxanes (e.g., cyclopentasiloxane) and dimethiconoles, alkyl methicones, alkyl dimethicones, dimethicone copolyols, amino-functional silicones (e.g., amodimethicone, trimethylsilyloxyamodimethicone) and amphoteric silicones (e.g., cetyl PEG/PPG-15/15 butyl ether dimethicone, and bis-PEG-18 methyl ether dimethyl silane).

Oily and oil-soluble extracts of plant materials such as flowers and herbs. This comprises a wide range of materials, with some non-limiting examples including extracts of rosemary, green, white or black tea, orchid, grape seed, sage, soybean, echinacea, arnica, rosehip, olive, artichoke. Further plant-extracted oil-soluble components such as lycopene and other mixed carotenoids, capsaicin and capsaicinoids, polyphenols (e.g., rosmarinic acid), terpenes and terpenoids, oleoresins.

Examples of oil-soluble dyes include, but are not limited to, Green 6 (CI 61570), Red 17 (CI 26100), Violet 2 (CI 60725) and Yellow 11 (CI 47000). Examples of oil-dispersible pigments include, but are not limited to Beta Carotene (CI 40800), Chromium Hydroxide Green (CI 77289), Chromium Oxide Green (CI 77288), Ferric Ferrocyanide (CI 77510), Iron Oxides (CI 77491, 77492 77499), Pigment Blue 15 (CI74160), Pigment Green 7 (CI 74260), Pigment Red 5 (CI 12490), Red 30 (CI 73360), Titanium Dioxide (CI 77891) and Ultramarines (CI 77007). Oil soluble pharmaceutical actives such as insect repellants (examples comprise N,N-Diethyl-meta-toluamide, IR3535, Icaridin, Picaridin, Saltidin, Citronella, Permethrin, Neem oil and Lemon Eucalyptus) and drug substances for the dermatological treatment of conditions of skin, hair and nails. This may comprise, but is not limited to, topical anaesthetics, anti-fungal, anti-bacterial, anti-viral, anti-dandruff, anti-acne and anti-inflammatory agents (steroidal and non-steroidal).

Examples of vitamin and derivatives include tocopherol, tocopheryl acetate, retinol, retinyl palmitate, ascorbyl palmitate, niacinamide, beta carotene.

The fragrances suitable for use in this invention include without limitation, any combination of perfumes, flavors, essential oils, sensates and plant extract or mixture thereof that is capable of being encapsulated in accordance with the present application. A list of suitable fragrances is provided in U.S. Pat. Nos. 4,534,891, 5,112,688, 5,145,842, 6,194,375, 20110020416 and PCT application Nos. WO2009153695 and WO2010/044834 and Perfumes Cosmetics and Soaps, Second Edition, edited by W. A. Poucher, 1959. Each of the foregoing documents is incorporated herein by reference in its entirety.

Typical representative perfume and sensate components include, but are not limited to, linalool, coumarin, geraniol, citral, limonene, citronellol, eugenol, cinnamal, cinnamyl alcohol, benzyl salicylate, menthol, menthyl lactate, eucalyptol, thymol, methyl salicylate, methylfuran, menthone, cinnamaldehyde.

Typical representative examples for essential oils include, but are not limited to, orange, lavender, peppermint, lemon, pine, rosemary, rose, jasmine, tea tree, lemon grass, bergamot, basil, spearmint, juniper, clove, aniseed, fennel, cypress, fir, black pepper, sandalwood, cedarwood, rosewood, cardamom, cinnamon, corander, eucalyptus, geranium, ginger, chamomile, grapefruit, neroli, petitgrain, thyme, vetiver and ylang ylang.

Non-limiting examples of phase change materials include n-octacosane, n-heptacosane, n-hexacosane, n-pentacosane n-tetracosane, n-tricosane, n-docosane, n-heneicosane, n-eicosane, n-nonadecane, n-octadecane, n-heptadecane, n-hexadecane, n-pentadecane, n-tetradecane and n-tridecane.

Chemical and physical sunscreens/UV filters, e.g., 3-Benzylidene Camphor, 4-Methylbenzylidene camphor, Aminobenzoic acid (PABA), Avobenzone, Benzophenone 4 (Sulisobenzone), Benzophenone 5, Benzophenone 8, Benzophenone-3, Benzylidene camphor sulfonic acid, Bisethylhexyloxyphenol methoxyphenol triazine (Escalol S), Butyl methoxy dibenzoylmethane, Camphor benzalkonium methosulfate, Cinoxate, Diethylamino hydroxybenzoyl hexyl benzoate, Dioxybenzone, Disodium phenyl dibenzimidazole tetrasulfonate, Drometrizole trisiloxane, Ensulizole, Ethylhexyl dimethyl PABA, Ethylhexyl methoxycinnamate, Ethylhexyl salicylate, Ethylhexyl triazone, Homosalate, Isoamyl p-methoxycinnamate, Meradimate, Menthyl anthranilate, Methylene bis-benzotriazolyltetramethylbutylphenol/Bisoctrizole (Tinosorb M), Octocrylene, Octinoxate, PEG-25 PABA, Octisalate, Oxybenzone, Padimate O, Phenylbenzimidazole sulfonic acid, Polyacrylamidomethyl Benzylidene Camphor, Polysilicone-15, TEA-salicylate, Terephthalylidene dicamphor sulfonic acid, Titanium dioxide, Trolamine Salicylate and zinc oxide.

Hair treatment materials, other than those covered in the previous ingredient list. This includes cationic conditioning agents comprising tertiary and quaternary amino groups (e.g., quaternium-70, quaternium-80, stearamidopropyl dimethylamine, behentrimonium methosulfate, dicocodimonium chloride, dicetyldimonium chloride, distearyldimonium chloride hydroxyethyl cetyldimonium phosphate). Further, UV and color protectants (e.g., dimethylpabamidopropyl laurdimonium tosylate), heat protectants and styling polymers (e.g., vinyl pyrrolidone and vinylcaprolactam derivatives, such as PVP vinyl Caprolactam/DMAPA Acrylates Copolymer).

Further include oil-soluble polymeric materials which have film-forming properties on skin and hair, such as VP/Hexadecene Copolymer, Tricontanyl PVP and VP/Eicosene Copolymer.

Additionally, the oil-soluble cosmetic or personal care actives, which are used for the conditioning or cosmetic treatment of skin, hair or nails are listed extensively and typically covered in IP.com publications IPCOM000128968D published 23 Sep. 2005 and IPCOM000133874D published 13 Feb. 2006, the contents of which are hereby incorporated by reference.

In one embodiment, microcapsules described herein may be incorporated in personal care compositions. Personal care compositions include, but are not limited to, cosmetics, drug delivery systems, hair, oil, pharmaceuticals, pigment dispersions, preservative compositions, including those to alter the color and appearance of the skin, sun and tissue regeneration scaffolds. Other personal care compositions include, but are not limited to, modified natural oils for increased flexibility in styling, durable styling, increased humidity resistance for hair, skin and color cosmetics, sun care, water proof/resistance, wear resistance, shower gels, shampoos, and thermal protecting/enhancing compositions. Dental personal care compositions include denture adhesives, toothpastes, mouth washes, chewing gums and the like.

Pharmaceutical compositions include peroral and topical dosage forms, such as tablets, pellets, capsules, dermatological products (creams, gels, ointments, sprays, lotions, and foams), transdermal patches and the like.

In one embodiment, the microcapsules may be used in conjunction with agrochemicals which are listed extensively in the ISP assigned U.S. Pat. No. 5,389,688, incorporated herein by reference in its entirety.

In one embodiment, the microcapsules may be used to incorporate actives such as fabric conditioners, liquid laundering detergents, powdered laundering detergents, dish washing detergents, hard surface cleaners, incorporation onto textiles both coatings and in-fiber, air sprays, paper coatings, household cleaners and products.

In one embodiment, the hydrogel microcapsules of the invention can be advantageously used in controlling perfume release in fragrance consumer products. There is a considerable improvement in longevity and intensity of the encapsulated perfume in actual use. Examples of consumer products comprising perfume microcapsules according to certain aspects of the present application may fall into product group categories of laundering detergents, cosmetics, personal care products, dish washing detergents and house cleaners. More specific examples of consumer products include fabric conditioners, liquid/powdered laundering detergents, dish washing detergents, hair shampoos, hair conditioners, hair styling gels, soaps, body washes, shower gels, all-purpose cleaners including hard surface cleaners, carpet cleaners, body lotions, antiperspirant/deodorants and spray-able products.

In another embodiment, the application relates to a method for producing fragrance loaded microcapsules with improved substantivity for incorporation into, (i) laundry detergents; (ii) fabric softener compositions; and (iii) drier-added fabric softener articles, these when deposited on fabrics during laundry treatment and capable of remaining on the textile following initial application and which is capable of later being sheared by the application of mechanical force. Accordingly, the encapsulated fragrance provides a "burst" of fragrance during wear due to breakage of the capsule wall.

Alternatively, the fragrance microcapsules of the present application can be formulated into solid fabric care compositions with polysaccharides such as sugars according to the procedure described in US Patent No 20011/0082066, the contents of which are hereby incorporated by reference. The solid fabric care products can be used for delivering fragrances onto the textile articles during the washing/cleaning cycle and subsequently the laundered textiles have beneficial fragrance odor profile during the wear.

Alternatively, the fragrance microcapsules can be incorporated in 2-in-1 powdered detergent and conditioner compositions according to the processes described in U.S. Pat. Nos. 4,698,167 and 5,540,850 and also crystalline laundry additives as described in the US application 2011/97369 and PCT WO 2010/000558, which are incorporated herein by reference.

For some embodiments, it may be preferred to add one or more preservatives and/or antimicrobial agents in the delivery matrix in addition to the respective actives, such as, but not limited to, benzoic acid, sorbic acid, dehydroacetic acid, piroctone olamine, DMDM hydnatoin, IPBC, triclosan, bronopol, isothiazolinones, parabens, phenoxyethanol, and combination thereof.

In another embodiment, the lipophilic core material may be a phase change material or mixtures for temperature control exhibiting melting temperature from −20° C. to 100° C. include linear or branched hydrocarbons or fatty esters or mixtures of different chain lengths and melting points. The microcapsules containing the phase change material lipophilic core material can be coated, sprayed or incorporated into suitable materials such as textile fibers such as cotton during the spinning process or coated directly onto textiles or incorporated into building construction material for example bricks, gypsum, to allow temperature control by use of latent heat of fusion.

It is further contemplated that microcapsules of the present application can be used in the construction industry in conjunction with cements, plaster boards, breeze blocks, chipboards, heat transfer fluids, sealants, adhesives etc. The lipophilic core material can be a phase change material, biocides, flame retardant, catalyst, epoxy resins etc.

Also contemplated are automotive applications including such encapsulated phase change material in the coolant systems, encapsulated lubricant additives such as anti-wear additives in engine oils and encapsulated UV absorbers for car coatings.

The microcapsules described herein may also be used in conjunction with additives used in plastics such as flame retardants, catalysts, pigments, light stabilizers, UV absorbers which can be encapsulated to allow higher compatibilities, longevity and self-healing of the plastic material. Particularly, the lipophilic core material can be catalyst for self-healing, UV absorber for protection, thermochromic material for colour change in coating industry.

The microencapsules may also be used in oilfield applications. The microcapsules may contain a lipophilic oilfield chemical core such as corrosion inhibitors, scale inhibitors, oxidizing agents, crosslinking agents, catalysts, acidizing agents, biocides, demulsifiers, enzymes, polymers, lubricants, shale inhibitors, solvents, and surfactants. The encapsulated oil field chemicals can be applied advantageously at the different petroleum extraction stages from drilling, cementing, stimulation to production and enhanced oil recovery. The release mechanisms of delivery of the oilfield chemical can be by temperature, dilution, pH and shear at the relevant points of applications.

The corrosion inhibitors may be selected from the group consisting of carboxylic acids and derivatives such as aliphatic fatty acid derivatives, imidazolines and derivatives; including amides, quaternary ammonium salts, rosin derivatives, amines, pyridine compounds, trithione compounds, heterocyclic sulfur compounds, quinoline compounds, or salts, quats, or polymers of any of these, and mixtures thereof. For example, suitable inhibitors include primary, secondary, and tertiary monoamines; diamines; amides; polyethoxylated amines, diamines or amides; salts of such materials; and amphoteric compounds. Still other examples include imidazolines having both straight and branched alkyl chains, phosphate esters, and sulfur containing compounds.

Lipophilic scale inhibitors include those based on phosphate esters, and polyacrylates.

Examples of oxidizing agents include inorganic or organic peroxides such as calcium peroxide, magnesium peroxides and lauryl peroxides.

Microcapsules can be supplied as dried powder form or in aqueous solution as a dispersion of hydrogel microcapsules. The powdered form may be obtained by spray drying or filtration of the aqueous form. It is contemplated that all of these material can be used with optional post coating material which may further comprise a post addition of a polymeric coating to improve its deposition. This optional coating also constitutes a means to improve and control the deposition of capsules onto a substrate, which is particularly useful for an application in some functional products such as shampoos, fabric softeners and laundering detergents.

Examples of particularly useful coating materials include cationic polymers such as polyvinyl pyrrolidone (PVP) copolymers (Gafquat HS-100, Styleze CC-10, Styleze W-20, Aqua Style 300 all available from ISP), cationic cellulose polymers, cationic guars, cationic acrylate copolymers, chitosan, DADMAC (diallyldimethyl ammonium chloride) copolymers and polyethylene imines The delivery system of the invention is prepared by a process comprising mixing directly the hydrogel microcapsules into surfactant containing products such as body rinse off products, shampoos, fabric conditioners, laundering detergents at required dose concentrations. The microcapsules remain uniformly suspended in the liquid surfactant products by addition of suitable rheology modifiers. In the case of powdered products, the aqueous microcapsule dispersion may be spray dried and granulated before mixing into the powdered mixture. In some instances, the microcapsules can be added as the last step before coating, spraying or incorporation onto suitable materials such as textile fibers, coated textiles and construction products.

The following non-limiting examples further illustrate the certain aspects of the present invention.

EXAMPLES

Example 1

Solubility of Amine Monomers of Formula I in Different Oils

The solubility of various amine methacrylate monomers such as diethylaminoethyl methacrylate (DEAEMA ex-Mitsubishi Rayon), Diisopropylaminoethyl methacrylate (DPAEMA ex-Aldrich), dimethylaminoethyl methacrylate (DMAEMA Mitsubishi Rayon) and tertiary-butylaminoethyl methacrylate (tBAEMA ex-Arkema) were determined in isopropyl myristate (fatty ester available from Stearinerie Dubois), mineral white oil (Carnation oil available from Sonneborn Inc USA) and Bodacious K/62930 fragrance (multi-component mixture of natural and synthetic fragrances available from Robertet Ltd U.K.).

The respective amine monomer was mixed with the selected oil from 0.1% weight to 99.9% weight. In all cases, the formed mixtures were single one phase, homogeneous and transparently clear. The result illustrates that all the amine monomers represented by Formula 1 are completely oil soluble at all proportions.

Example 2

Solubility of Amine Monomers of Formula I in Water

The solubility of various amine methacrylate monomers in water was estimated by mixing separately into 100 g of deionised water varying amount of the respective amine monomer (0.1 g, 0.2 g, 0.3 g, 0.4 g, 0.5 g, 1.0 g. 1.5 g, 2.0 g, 2.5 g 5.0 g, 7.5 g, 10.0 g 12.5 g and 15.0 g) in a measuring cylinder and noting the solubility. The insolubility point was reached when a distinct two separate layers was observed. The results are summarized in Table 2.

TABLE 2

Estimation of solubility of amine monomer of Formula 1 in water

| Amine monomer/100 gm water (W/W) | DEAEMA | DPAEMA | DMAEMA | TBAEMA |
| --- | --- | --- | --- | --- |
| 0.1 g | soluble | soluble | soluble | soluble |
| 0.2 g | insoluble | insoluble | soluble | soluble |
| 0.3 g | insoluble | insoluble | soluble | soluble |
| 0.4 g | insoluble | insoluble | soluble | soluble |
| 0.5 g | insoluble | insoluble | soluble | soluble |
| 1.0 g | insoluble | insoluble | soluble | soluble |
| 1.5 g | insoluble | insoluble | soluble | soluble |
| 2.0 g | insoluble | insoluble | soluble | insoluble |
| 2.5 g | insoluble | insoluble | soluble | insoluble |
| 5.0 g | insoluble | insoluble | soluble | insoluble |
| 7.5 g | insoluble | insoluble | soluble | insoluble |
| 10.0 g | insoluble | insoluble | soluble | insoluble |
| 12.5 g | insoluble | insoluble | insoluble | insoluble |
| 15.0 g | insoluble | insoluble | insoluble | insoluble |

Results of Table 2 illustrates amine monomers as represented by Formula I had very low water solubility. The DEAEMA and DPAEMA have low solubility in water of less than 0.2 g/100 g water; tBAEMA is less than 2 g/100 g. This value is in agreement with the published literature value of 18 g/liter; (Reference: Material Safety Data Sheet from Arkema Inc for Norsocryl, t-Butylaminoethyl methacrylate).

Example 3

Preparation of 60% Weight DEAEMA and 40% Weight BDDA Microcapsule Shell

Experiment 1

An internal phase was prepared by dissolving 15.7 g of DEAEMA monomer and 10.4 g of butane diol diacrylate into 126.4 g of isopropyl myristate. Into this oil mixture was dissolved 0.52 g of lauryl peroxide.

Separately, an external phase was prepared by dissolving 7.0 g of polyvinyl alcohol (ex-Nippon Gohsei, Gohsenol GH-20R) into 278.9 g deionised water by heating to 85° C. and then cooling back to room temperature.

The internal phase was added to the external oil phase under a high shear mixer (Silverson LR4) to form an oil-in-water emulsion having a mean particle size of 4 μm. The formed emulsion was transferred to a 700 ml reaction flask submerged in a thermostatic bath and mechanically stirred. The emulsion was deoxygenated by bubbling with nitrogen for 30 minutes. After, purging with nitrogen, the emulsion was warmed to 80° C. to induce the thermal polymerization. A mild exotherm was observed from 80° C. to 85° C. over 20 minutes. The mixture was left polymerising for total of 2 hours. After, this period, 0.1 g of ammonium persulphate was added to consume any residual impurities of monomers to below 100 ppm. Next, the aqueous dispersion of microcapsules was cooled to room temperature and 5.1 g of glacial acetic acid dissolved in 75 g water added to form the cationized hydrogel microcapsules.

The final product form is a smooth aqueous dispersion of microcapsules in water. Under the light microscope, distinct microcapsules having swollen capsule shells are clearly visible with mean particle size of 5.4 μm.

Example 4

Preparation of 80% Weight DEAEMA and 20% Weight BDDA Microcapsule Shell

Experiment 2

The procedure of Example 3 was followed with exception that the internal phase comprised of 20.9 g of DEAEMA, 5.2 g BDDA and 126.1 g isopropyl myristate. The formed aqueous microcapsule dispersion was cationized by adding 6.8 g of glacial acetic acid dissolved in 100 g water.

The resulting product comprised an aqueous dispersion of microcapsules with mean particle size of 7.5 µm having a greater degree of water swollen capsule shell than those of Example 3.

Example 5

Preparation of 80% Weight DEAEMA and 20% Weight BDDA Microcapsule Shell Containing Fragrances in the Microcapsule Core

Experiment 3

The procedure of Example 4 was followed with exception that the internal phase comprised 20.9 g of DEAEMA, 5.2 g BDDA and 126.1 g Bodacious K/62930 fragrance oil mixture.

The resulting product comprised an aqueous dispersion of microcapsules with mean particle size of 7.9 µm with water swollen capsule shell.

Example 6

Preparation of 80% Weight DEAEMA and 20% Weight BDDA Microcapsule Shell Containing Fragrances in the Microcapsule Core

Experiment 4

The procedure of Example 5 was followed with exception that the microcapsule dispersion at room temperature was post treated with 100 g of water and 14.2 g of dimethyl sulphate to form the cationic hydrogel shell microcapsules instead of glacial acetic acid.

The resulting product comprised of aqueous dispersion of microcapsules with mean particle size of 9.1 µm with water swollen capsule shell.

Example 7

Control Experiment: Preparation of Fragrance Microcapsules with Water Soluble Quaternized Form of DEAEMA Example 6 above was followed except the 20.9 g of DEAEMA monomer was quaternized with 14.2 g of dimethylsulphate to form Diethylaminoethyl methacrylate dimethyl sulphate quaternary ammonium form (DEAEMA Quat DMS). This form of the monomer is completely water soluble and insoluble in oils.

On thermal polymerization at 80° C. to form the microcapsule shell containing the fragrance oil mixture, the total reaction thickened up to a solid mass and the required microcapsules were not formed. This example clearly shows that use of high proportion of water soluble DEAEMA Quat DMS to form the capsule shell, it is possible to form the desired microcapsules. It is concluded that bulk of the water soluble DEAEMA Quat DMS monomer polymerizes in the external surrounding water phase to form a water soluble polymer and it does not take part in forming the desired capsule shell.

Example 8

Preparation of Microcapsules with DMAEMA, DPAEMA and TBAEMA Amine Monomers

Experiment No. 5, 6 and 7

Example 3 was repeated with the exception of instead of using DEAEMA monomer, three other oil soluble listed in Table 3 were used and the formed microcapsule shell cationized with this given amount of glacial acetic acid.

TABLE 3

List of amine monomers and cationizing treatment conditions

| Experiment No. | Amine Monomer | Cationizing Treatment |
|---|---|---|
| 5 | Dimethylaminoethyl methacrylate (DMAEMA) | 6.0 g acetic acid in 75 g water |
| 6 | Diisopropylaminoethyl methacrylate (DPAEMA) | 4.4 g acetic acid in 75 g water |
| 7 | Tertiarybutylaminoethyl methacrylate (TBAEMA) | 5.1 g acetic acid in 75 g water |

All three amine monomers gave aqueous microcapsule dispersions and under the light microscope very distinct hydrogel capsule shells were clearly visible.

Example 9

Preparation of Microcapsules with High Contents of TBAEMA Monomers in Capsule Shell

Experiment No. 7, 8, 9, 10 and 11

A series of cationic hydrogel microcapsules were prepared with the monomer mixture comprising of varying ratios of TBAEMA: BDDA from 60:40% weight to 98:2% weight as given in Table 4 using the procedure described in Example 3 with the exception of the monomer composition.

TABLE 4

Microcapsule Shell comprising varying ration of TBAEMA/BDDA:

| Experiment No | TBAEMA:BDDA Ratio | Cationizing Treatment |
|---|---|---|
| 7 | 60:40 | 5.1 g acetic acid in 75 g water |
| 8 | 80:10 | 6.8 g acetic acid in 90 g water |
| 9 | 90:10 | 7.6 g acetic acid in 100 g water |
| 10 | 95:5 | 8.0 g acetic acid in 120 g water |
| 11 | 98:2 | 8.3 g acetic acid in 120 g water |

The light microscope examination of the microcapsule showed progressing increasing size of the outer hydrogel capsule shell. Microcapsules formed from Experiments 10 and 11 had significant swelling of the outer capsule shell and were greater in volume by at least three times compared to the encapsulated isopropyl myristate core.

Example 10

Control Experiment: Preparation of Microcapsules with Capsule Shell Having Monomer Mixture Composition of 45:55; TBAEMA: BBDA

Experiment No. 12 and 13

Two microcapsule samples were prepared following Example 3 with the exception that the monomer mixture comprised of 45% weight of TBAEMA and 55% weight BDDA and two different core materials. The cores are listed in Table 5 along with the respective half heights.

The aqueous microcapsules formed were analyzed by thermo gravimetric analysis to determine the half height values; the half height refers to the temperature at which half the weight of the capsule is lost according to the method described in US20070224899, which is incorporated herein for reference only.

The results of TGA analysis illustrates that microcapsules prepared according to present invention have much lower half-height results compared to those prepared according to US Patent application No. 20070224899 (Ciba) (Example 6).

TABLE 5

Results of TGA analysis of Experiments 12 and 13

| Experiment No | Core material | Half-Height (° C.) |
|---|---|---|
| 12 | Isopropyl myristate | 294 |
| 13 | Bodacious K/62930 fragrance | 256 |

Example 11

Conversion of Microcapsules to Dry Powdered Form

Experiment 14

The aqueous dispersion of Example 3 was spray dried using Buchi Mini-Spray Drier B-290 with inlet temperature of 180° C. and outlet temperature of 90° C. A dried free flowing powder was obtained. Under the light microcapsules agglomerates of microcapsules were clearly apparent.

Example 12

Comparative Experiment to Show Substantivity of Cationized Hydrogel Microcapsules VS Conventional Melamine Formaldehyde Shell Microcapsule A blue colored isopropyl myristate oil phase was prepared by dispersing 4% by weight of Sicomet Blue P74160 (ex-BASF) into the fatty ester with a high shear mixer (Silverson model LR4). The resulting blue colored oil phase was encapsulated by two different procedures to form Samples A and B Preparation of Sample A—

Example 3 was repeated with the exception the blue colored isopropyl myristate oil phase was used instead of the isopropyl myristate as supplied. The final sample obtained was a blue colored aqueous dispersion of microcapsules. Under the light microscope, distinct blue colored fatty ester core microcapsules were clearly seen with an outer hydrogel shell.

15 g of the blue colored microcapsules (Sample A) was added to 100 g of commercially available fragrance free fabric conditioner Ultra Downy Free & Sensitive (ex—P&G USA) and agitated for 2 hours under mechanical stirring. The resulting 'Mixture X' was used for the substantivity test.

Preparation of Sample B—

The same batch of the blue colored isopropyl myristate oil phase was microencapsulated using melamine formaldehyde encapsulation procedure. An aqueous phase was prepared by diluting 60 g of 20% copolymer of acrylamide and sodium acrylate (Alcapsol 144 ex-Ciba) with 200 g water. To this diluted polymer solution was added 25 g of 70% melamine formaldehyde resin (Beetle Resin PT336 Ex-British Industrial Plastics Ltd) followed by addition of 3.6 g of 85% formic acid. Next, the aqueous phase was warmed to 30° C. and maintained at this temperature for 75 minutes.

The above 4% blue colored isopropyl myristate oil phase (140 g) was added to the warm aqueous phase under a high shear mixture to form an oil-in-water emulsion. The high shearing mixing was continued until the mean particle sizes of the dispersed oil droplets were about 5 μm. The formed oil-in-water emulsion was then transferred to a reaction flask and warmed to 60° C. under mechanical agitation. The reaction flask content was maintained at 60° C. temperature for 4 hours to form the melamine formaldehyde shell microcapsules. After this reaction, the product cooled to room temperature and adjusted to pH 8.0 by addition of 20% sodium hydroxide solution.

The final sample was an aqueous dispersion of around 35% by weight microcapsules having a blued colored inner core and melamine formaldehyde polymer shell. Under the light microscope examination, blue colored microcapsules with distorted morphology were clearly observed.

15 g of the prepared blue colored microcapsules having the melamine polymer shell was added to 100 g of commercially available fragrance free fabric conditioner Ultra Downy Free & Sensitive (ex—P&G USA) and agitated for 2 hour under mechanical stirring. The resulting 'Mixture Y' was used for the substantivity test.

Colour Measurements of the Cotton and Polyester Swatches

The blue colour intensity measured (dE CMC) on the respective cotton/polyester swatches are summarised in Table 6 for the two different microcapsule samples tested (Sample A and B).

TABLE 6

Colour Measurements (dE CMC) of the Test Swatches

| Sample tested for measuring blue colour on the swatches | Cotton swatches dE CMC (average) | Polyester swatches dE CMC (average) |
|---|---|---|
| Sample A, microcapsules according to invention | 5.23 | 10.52 |
| Sample B, microcapsules with melamine polymer shell | 2.10 | 5.95 |

The higher blue coloration (dE CMC) of the test swatches with the fabric conditioner Mixture X containing the present invention microcapsules (Sample A) demonstrates the higher substantivity onto both cotton and polyester substrates compared to conventional melamine polymer shell microcapsules (Sample B).

Visual examination showed that the swatches from test Solution I were substantially colored blue whereas from Solution II were just faintly coloured blue. The test swatches were examined under the light microscope and it was clearly apparent that significant amount of microcapsules of Sample A had adhered to the both different swatches compared to those treated with Sample B.

Substantivity Test

For each experiment, 1 litre of tap water (weighed as 1000±10 g) was added into a 2000 ml beaker; the water temperature was between 20-25° C. An overhead stirrer was inserted (bottom edge of blade ca. 3-4 cm above bottom of beaker) and adjusted to a speed of 100±2 rpm.

Solution I—1000 g of tap water in a 2000 ml beaker. To this was added 2.3 g of Mixture X.

Solution II—1000 g of tap water in a 2000 ml beaker. To this was added 2.3 g of Mixture Y.

When the respective test solution was evenly dispersed, 6 dry fabric swatches (Prewashed Cotton #400 or Polyester #777 available from Scientific Services S/D Inc., PO Box 778, Sparrowbush, N.Y. 12780, USA) were added to each beaker. The stirring at 100 rpm was continued for 10 minutes.

After this time, the swatches were removed into a large weighing boat. The liquor was discarded, and the beaker rinsed and refilled with 1 litre of fresh tap water at room temperature. The fabric swatches were added back into the clean water and stirred at 100 rpm for another 3 minutes. The swatches were taken out, gently squeezed to remove excess water. Next, the swatches were hung up on a laundry line to air-dry overnight, keeping the swatches as straight as possible (peg in one corner). Swatches were marked to identify the corresponding samples.

On the following day, the air-dried fabric swatches were analysed by measuring the blue colour intensity, visual assessment and light microscopic examination.

The blue colour intensity on the fabric swatches was measured using a Hunterlab Colorquest XE instrument. The 6 swatches of the same material from each experiment were stacked one upon the other. This was to avoid background colour shining through the fabric. Clean, untreated fabric swatches (stack of 6) were used as a reference. Cotton samples are measured against cotton reference and Polyester samples against polyester reference For each sample stack, 18 individual measurements were carried out as follows: The stack was clamped to the instrument and moved after each measurement, until 3 random points have been measured on the top sheet. The top sheet was then peeled off and moved to the back of the stack. 3 random points were measured on the second sheet, which was then moved to the back, and the same with the following sheets.

The above tests clearly demonstrate that the cationic hydrogel microcapsules of present invention have enhanced substantively compared to the conventional melamine formaldehyde shell microcapsules.

Example 13

Preparation of Fragrance Microcapsules

An internal oil phase was prepared by dissolving 15.7 g tBAEMA monomer and 10.4 g of butane diol diacrylate bifunctional monomer into 86.4 g of Bodacious fragrance K/62930 (ex-Robertet Ltd UK). To this fragrance/monomer mixture was dissolved 40.0 g of isopropyl myristate and 1.04 g of Vazo 67 thermal initiator (ex-Du Pont). The above internal phase was added to an external aqueous phase comprising of 7.0 g polyvinyl alcohol (ex-Nippon Gohsei, Gohsenol GH-20R) and 278.9 g deionised water under a high shear mixer (Silverson LR4) to form an oil-in-water emulsion having a mean particle size diameter of oil droplets of around 4 microns.

The resulting oil-in-emulsion was deoxygenated with nitrogen and polymerised according to the process conditions described in Example 3.

The fragrance product resulting is a smooth aqueous dispersion of microcapsules in water @ 35% total solids containing 20.0% encapsulated Bodacious fragrance. Under scanning electron microscopy (SEM) examination, discrete microcapsules particles of mean particle sizes of 4 microns were clearly observed having a slight distorted particle morphology; indicative of polymeric capsule shell formation and confirmation of effective encapsulation. Under the SEM conditions, it is known that if no or poorly microcapsule shell is formed, no microcapsule particles are visible due to volatilities of the internal oil phase.

To form the cationized acetate salt form of the microcapsules, the above aqueous microcapsule dispersion was cationized by addition of 21.3 g of 80% acetic acid. The pH of the resulting aqueous dispersion was pH 4.0. Under the light microscope examination, the presence of the hydrogel capsule shell was clearly apparent.

Example 14

Measurement of Cationic Charge on Microcapsules

The preparation of the Bodacious microcapsules of Example 13 was repeated but after the polymerisation step the acetic acid is not added to form the cationic salt form. This sample containing microcapsules in the free base form was divided into four separate samples. Each sample dispersion was treated differently to cationised the microcapsules fully with the required reagent as summarized in Table 7. The zeta potential of each sample was measured by diluting to $1/100$ and $1/1000$ with water and then measurement of particle charge using Zetasizser Nano ZS available from Malvern Instruments.

TABLE 7

Zeta potentials of microcapsules cationized with different reagents.

| Sample No | Cationising Agent | Zeta Potential (mV) 1/100 Dilution | Zeta Potential (mV) 1/1000 Dilution |
|---|---|---|---|
| I | None | −1.610 | −3.580 |
| II | Acetic acid | +1.350 | +4.640 |
| III | Sulphuric acid | +0.825 | +1.610 |
| IV | Dimethyl Sulphate | +1.500 | +5.370 |

From the zeta potential measurements of the microcapsules cationized with different reagents and the two levels of dilutions. The microcapsules in the free base form have a negative charged as prepared but on cationisation with acid or cationising reagent are converted into positively charged microcapsule particles. Furthermore, the positive charge on the microcapsules increases on further dilution thus illustrating the presence of the cationized hydrogel microcapsule shell which is the essential feature of this invention.

Example 15

Stability of Fragrance Microcapsules of Example 13 in Surfactant Solutions

The Bodacious fragrance microcapsules (10 g) of Example 13 were added into two different separate surfactant solutions (90 g), (i) sodium lauryl sulphate (anionic surfactant) at 10% w/w and (ii) PEG-5 cocomonium methosulphate (cationic surfactant) at 1% w/w. The integrity/physical stability of the microcapsules was assessed by storing the resulting mixture at room temperature and 40° C. After 4, 8 and 12 weeks, the microcapsules/surfactant mixtures sub-samples were examined visually and by light microscopy. At all time points, the samples of both storage temperatures contained intact microcapsule particles with a distinct internal phase and a slightly swollen microcapsule shell. No visual changes were observed.

Each of the above aged microcapsules/surfactant mixture (5.0 g) was diluted with 100 g of tap water and magnetically stirred for 10 minutes. Under light microscopy examination, distinct swollen microcapsules were clearly observed. It is inferred that the fragrance microcapsules remained stable and intact in the surfactant solutions due to the higher ionic strength of the aqueous mixture and on dilution the microcapsule shell swell due to lower ionic strength of the surrounding aqueous medium.

The above example demonstrates the fragrance microcapsules formed from present invention remain intact in surfactant solutions commonly used in formulating detergents, cleaning and personal care products.

Example 16

Encapsulation of UV Absorber (Octocrylene)

An internal oil phase was prepared by dissolving 1.56 g of Vazo 67 thermal initiator (ex-Du Pont) into a monomer mixture comprising of 15.7 g tBAEMA monomer and 10.4 g of butane diol diacrylate bifunctional monomer. To this monomer mixture was dissolved 126.4 g of Escalol 597 (Octocrylene, available from ex-International Specialty Products). The above internal phase was added to an external aqueous phase comprising of 7.0 g polyvinyl alcohol (ex-Nippon Gohsei, Gohsenol GH-20R) and 278.9 g deionised water under a high shear mixer (Silverson LR4) to form an oil-in-water emulsion having a mean particle size diameter of oil droplets of around 5 microns.

The resulting oil-in-emulsion was deoxygenated with nitrogen and polymerised according to the process conditions described in Example 3.

The microcapsule product formed is a smooth aqueous dispersion of microcapsules in water @ 35% total solids containing encapsulated UV absorber. Under light microscope examination, discrete microcapsules particles of mean particle sizes of 6 microns were clearly observed.

Example 17

Microcapsules in Hair Conditioner

TABLE 8

| Microcapsules in Hair Conditioner | |
|---|---|
| Material | % Weight |
| Disodium EDTA | 0.02 |
| Hydroxyethylcellulose | 0.50 |
| Butyrospermum Parkii (Shea Butter) | 10.00 |
| Caprylic/Capric Triglyceride | 5.00 |
| Behenyl Alcohol & Cetearyl Alcohol & Hydroxyethyl Cetearylamidopropyldimonium Chloride (ProLipid™ 161) | 5.00 |
| Cetearyl Alcohol | 3.00 |

TABLE 8-continued

| Microcapsules in Hair Conditioner | |
|---|---|
| Material | % Weight |
| Quaternium-22 (Ceraphyl® 60) | 2.00 |
| Fragrance Microcapsules of Example 13 | 2.50 |
| Preservative | q.s. |
| Deionised Water | q.s. ad 100% |

Example 18

Microcapsules in Shower Rinse-Off Product

TABLE 9

| Microcapsules in Shower Rinse-Off Product. | |
|---|---|
| Material | % Weight |
| Glycerin | 2.00 |
| Ammonium Laureth Sulfate 25% (Rhodapex EA-2) | 27.00 |
| Cocamidopropyl Betaine 30% (Mirataine CB) | 3.00 |
| Acrylates Copolymer (Carbopol Aqua SF-1) | 8.00 |
| $C_{12-15}$ Alkyl Lactate (Ceraphyl® 41) | 0.40 |
| Sodium Hydroxide | 0.34 |
| Fragrance Microcapsules of Example 13 | 3.75 |
| Preservative/Dye/Perfume | q.s. |
| Deionised Water | q.s. ad 100% |

Example 19

Encapsulation of Peppermint Oil

An internal oil phase was prepared by dissolving 19.2 g tBAEMA monomer and 19.2 g of butane diol diacrylate into 114.1 g of American Peppermint Oil. To this mixture was dissolved 1.56 g of Vazo 67 thermal initiator (ex-Du Pont).

Separately an external aqueous phase was prepared comprising 2.5 g of hydroxyethyl cellulose (ex-Ashland, Grade Natrosol 250G) and 297.5 g deionised water. This formed aqueous phase was transferred to a 700 ml reaction flask equipped with a mechanical agitator and nitrogen bubbler. The contents of the reaction flask were deoxygenated by bubbling nitrogen for 30 minutes. Once this aqueous phase was degassed, the above Peppermint Oil/Monomer internal phase was added to the reaction flask under mechanical agitation to form an oil-in-water suspension with a mean internal oil droplet particle sizes of 500 microns.

Next, the oil-in-water suspension was warmed to 80° C. to induce the polymerisation to form the microcapsules having peppermint has the internal phase. The reaction was continued for 6 hours at 80° C. to complete the capsule shell forming reaction. After, encapsulation, the peppermint oil microcapsules suspension in water was cooled to room temperature and the microcapsules filtered and re-suspended in fresh de-ionised water to form a 40% slurry of microcapsules in water.

Following are Non-Limiting Examples of Consumer Formulations Containing the Microcapsules of the Present Invention.

Example 20

Microcapsules in Fabric Softener

TABLE 10

Fabric Softener composition

| Material | % Weight |
|---|---|
| Cationic Surfactant (Esterquat) | 6.20 |
| Cationic liquid dispersion polymer (Jaypol ® 213) | 0.65 |
| Phosphoric Acid | 0.045 |
| Fragrance Microcapsules of Example 13 | 2.5 |
| Preservative/Dye | q.s. |
| Deionised Water | q.s. ad 100% |

Example 21

Microcapsules in Antiperspirant Stick

TABLE 11

Antiperspirant Stick composition

| Material | % Weight |
|---|---|
| Aluminium Chlorohydrate (Locron P) | 20.00 |
| Cetyl Alcohol | 18.00 |
| Stearic Acid | 18.00 |
| PVP (Poviderm ® SK3) | 1.00 |
| Spray Dried Microcapsules of Example 11 | 2.00 |
| Cyclopentasiloxane (Si-Tec ™ CM 040) | q.s. ad 100% |

Example 22

Microcapsules in Perfume-Impregnated Cloths or Wipes

The below suspension is sprayed onto a substrate and dried. Substrates may include woven or non-woven fabrics as used in personal care, household and hygiene products.

TABLE 12

Perfume-impregnated cloths or wipes composition

| Material | % Weight |
|---|---|
| Fragrance Microcapsules of Example 13 | 10.00 |
| Carboxymethyl cellulose | 0.50 |
| Deionised Water | q.s. ad 100% |

Clothes prepared according to above procedure were assessed for fragrance before and after rubbing the fabric. The clothes gave noticeably stronger perfume odor after rubbing, confirming that encapsulated fragrance is released "on demand" by mechanical breakage of the microcapsules.

Example 23

Microcapsules in Air Freshener/Room Spray

This formulation is used from a manual trigger spray dispenser. If used as an aerosol, propellant is added as needed.

TABLE 13

Air freshener composition

| Material | % Weight |
|---|---|
| Isopropyl alcohol | 5.00 |
| Lauryl Pyrrolidone (Surfadone ® LP-300) | 0.10 |
| Preservative, e.g. Nuosept ® 44 | q.s. |
| Fragrance Microcapsules of Example 13 | 2.50 |
| Deionised Water | q.s. ad 100% |

Example 24

Microcapsules in Moisturizing Cream

TABLE 14

Moisturizing cream composition

| Material | % Weight |
|---|---|
| Propylene Glycol | 3.00 |
| Acrylic Acid/VP Crosspolymer (UltraThix ™ P-100) | 1.10 |
| Sodium Hydroxide | 0.22 |
| Butyrospermum Parkii (Shea Butter) | 4.00 |
| C12-C15 Alkyl Lactate (Ceraphyl ® 41) | 4.00 |
| Glyceryl Stearate & Laureth-23 (Cerasynt ® 945) | 2.00 |
| Cetearyl Alcohol | 2.00 |
| Water & Glycerin & Glyceryl Acrylate/Acrylic Acid Copolymer & Cyclopentasiloxane & Dimethiconol & Laureth-23 (and) Phenoxyethanol) (Lubrasil ® II SB) | 3.00 |
| Fragrance Microcapsules of Example 13 | 1.00 |
| Preservative | q.s. |
| Deionised Water | q.s. ad 100% |

The invention has been described in detail with particular reference to particular embodiments thereof, but it will be understood that variations and modifications can be effected within the spirit and scope of the invention.

We claim:

1. A substantive cationized hydrogel microcapsule comprising a lipophilic core material and a polymeric shell material, wherein the polymeric shell consists of:
  a) 60 to 80% by weight of an oil soluble mono functional ethylenically unsaturated amine monomer that has a water solubility of less than 2.0 g/100 g of water at about 20° C., wherein the amine monomer is selected from Tertiary-butylaminoethyl methacrylate (TBAEMA), n-Butylaminoethyl methacrylate (NBAEMA), Diethylaminoethyl methacrylate (DEAEMA), Dimethylaminoethyl methacrylate (DMAEMA), Diisopropylaminoethyl methacrylate (DPAEMA), Dibutylaminoethyl methacrylate (DBAEMA), Dipropylaminoethyl methacrylate (DPAEMA), Tertiary pentylaminoethyl methacrylate (TPAEMA), Tertiary hexylaminoethyl methacrylate (THAEMA), Tertiarbutylaminopropyl methacrylate (TBAPMA), Diethylaminopropyl methacrylate (DEAPMA), and Dimethylaminopropyl methacrylate (DMAPMA); and
  b) 20 to 40% by weight of a polyfunctional ethylenically unsaturated monomer is selected from the group consisting of divinyl benzene, ethylene glycol di(meth)acrylate, di(ethylene glycol) di(meth)acrylate, triethylene glycol di(meth)acrylate, propylene glycol di(meth)

acrylate, 1,4-butanediol di(meth)acrylate, 1,6-hexanediol di(meth)acrylate, glycerol di(meth)acrylate, 1,3-butanediol di(meth)acrylate, neopentyl glycol di(meth)acrylate, 1,10-decanediol di(meth)acrylate, pentaerythritol tri(meth)acrylate, pentaerythritol tetra(meth)acrylate, dipentaerythritol hexa(meth)acrylate, triallylformal tri(meth)acrylate, allyl methacrylate, trimethylol propane tri(meth)acrylate, tributanediol di(meth)acrylate, PEG 200 di(meth)acrylate, PEG 400 di(meth)acrylate, PEG 600 di(meth)acrylate, 3-acryloyloxyglycol monoacrylate, triacryl formal, triallyl isocyanate, and triallyl isocyanurate;

wherein the amine groups on the polymeric shell are protonated or alkylated by treatment with a cationizing agent, wherein the cationizing agent is selected from the group consisting of an inorganic acid, an organic acid, a quaternizing agent, or a mixture thereof, wherein the microcapsule has a mean particle size of 1-2000 μm, wherein the microcapsule has % by weight of polymeric shell material of 6-20% by weight of the microcapsule, and wherein the microcapsules exhibit a half-height of less than 300° C.

2. The microcapsule according to claim 1, wherein the amine groups on the polymeric shell are alkylated with a quaternizing agent.

3. The microcapsule according to claim 1, wherein the lipophilic core material is selected from the group consisting of fragrances, UV absorbers, emollient oils, insecticides, phase change materials, dyes, detergents, printing inks, perfumes, silicone conditioners, shampoos, biocides, adhesives, corrosion inhibitors, anti-fouling agents, flavors, cosmetic actives, oxidizing agents, personal care actives, medicines, agrochemicals, fertilizers, fats, oils, nutrients, enzymes, liquid crystals, paints, rustproofing agents, recording materials, catalysts, chemical reactants, magnetic substances, and combination thereof.

4. The microcapsule according to claim 1, further comprising at least one polymeric stabilizer selected from the group consisting of cationic cellulose derivatives, quaternized gums, polyethylene imines, cationic polyacrylates, polyacrylamides, polyacrylates, gelatin, quaternized protein hydrolysates, quaternized amino silicones, hydroxyethyl cellulose, polyvinylpyrrolidone, poly vinyl alcohol, a styrene co-polymer with maleic anhydride or acrylic acid and combinations thereof.

5. The microcapsule according to claim 1, wherein the microcapsule has a mean particle size of 1-50 μm.

6. The microcapsule according to claim 1, wherein the microcapsule has a mean particle size of 1-20 μm.

7. The microcapsule according to claim 1, wherein the oil soluble mono functional ethylenically unsaturated amine monomer is selected from the group consisting of TBAEMA, DEAEMA, DMAEMA, and DPAEMA.

8. The microcapsule according to claim 1, wherein the polyfunctional ethylenically unsaturated monomer is 1,4 butanediol dimethacrylate.

* * * * *